United States Patent [19]

Phillips

[11] Patent Number: 5,263,969

[45] Date of Patent: Nov. 23, 1993

[54] TOOL FOR THE LAPAROSCOPIC INTRODUCTION OF A MESH PROSTHESIS

[76] Inventor: Edward H. Phillips, 712 N. Roxbury, Beverly Hills, Calif. 90210

[21] Appl. No.: 869,928

[22] Filed: Apr. 17, 1992

[51] Int. Cl.⁵ .................. A61F 13/00; A61F 15/00; A61F 2/00
[52] U.S. Cl. ........................ 606/213; 606/1; 606/151; 606/108; 623/11
[58] Field of Search .................. 604/93, 11–15, 604/104, 158, 166, 171; 606/1, 107, 110, 108, 113, 127, 138–147, 151–158, 170, 171, 213; 623/11; 128/887, 830

[56] References Cited

U.S. PATENT DOCUMENTS

| | | | |
|---|---|---|---|
| 4,832,055 | 5/1989 | Palestrant | 606/151 |
| 5,116,357 | 5/1992 | Eberbach | 606/151 |
| 5,122,155 | 6/1992 | Eberbach | 606/151 |
| 5,147,316 | 9/1992 | Castillenti | 604/164 |
| 5,147,374 | 9/1992 | Fernandez | 606/151 |

OTHER PUBLICATIONS

Toy-Smoot Laparoscopic Hernioplasty-Frederik Toy, Ray Smoot pp. 151-155 Surgical Laparoscopy and Endoscopy vol. 1, No. 3, 1991.

*Primary Examiner*—Stephen C. Pellegrino
*Assistant Examiner*—Glenn K. Dawson
*Attorney, Agent, or Firm*—Frederick Gotha

[57] ABSTRACT

A tool for inserting a mesh prosthesis into the retroperitoneal space in the laparoscopic repair of inquinal and femoral herniae is set forth which includes a housing having an axially extending passageway therethrough and a carriage member slidingly and telescopically carried by the housing and extending into the passageway. The carriage member has a holding chamber adjacent its distal end for holding the mesh prosthesis in a radially overlapped wound position. An axially extending slot in the carriage member communicates with the holding chamber to permit radial unwinding and passage of the mesh prosthesis from the holding chamber into the retroperitoneal space. The carriage member is slidably and rotatably mounted to the housing to permit axial extension and retraction of the holding chamber from the passageway into and from the retroperitoneal space.

16 Claims, 4 Drawing Sheets

TOOL FOR THE LAPAROSCOPIC INTRODUCTION OF A MESH PROSTHESIS

FIELD OF THE INVENTION

This invention relates to a surgical tool for the introduction of a mesh prosthesis into the retroperitoneal space to surgically repair inquinal or femoral herniae laparoscopically.

BACKGROUND OF THE INVENTION

In order to repair an inquinal or femoral heria laparoscopically, a retroperitoneal space is firt formed by the injection of carbon dioxide gas through a Veress needle positioned in the supbrapubic region. Thereafter, the peritoneum is swept from the posterior abdmoninal wall and a laparoscope is inserted into the retroperitoneal space. A mesh prosthesis is then introduced into the space through an abdominal trocar having a diameter of 5 mm to 10 mm; the mesh is wound in a radially overlappling fashion and pushed through the trocar by the surgeon. As the mesh emerges from the trocar into the operative space, the surgeon grasps the mesh with an appropriate grasper tool and thereafter unwinds the mesh and positions it to overlay the pelvis. The mesh is then sutured or fastened to the posterior abdominal wall which reinforces the wall at the site of the herination.

The unwinding of the mesh prosthesis after introduction into the operative space and the subsequent positioning of the mesh requires the manipulation of several grasping tools simultaneously and consumes a substantial amount of time thereby increasing the surgical risk involved. In addition, the suturing and fastening of the mesh intermittently disturbs the positioning of the mesh overlay thereby reqiring continued use of multiple grasping instruments which again delays the suturing or fastening of the mesh and increases the time of the operation.

SUMMARY OF THE INVENTION

There is, therefore, provided according to the present invention, a surgical tool for laparoscopically introducing a mesh prosthesis into the retroperitoneal space where the mesh is radially and overlappingly wound and retained in the chamber of a carriage member; the mesh may be fed from the chamber through an axially extending slot in the periphery of the carriage by appropriate rotation of the carriage after the leading edge of the mesh is selectively positioned and fastened to the abdominal wall. Thus, the complexity involved in the simultaneous manipulation to unwind and position the mesh prosthesis is substantially reduced resulting in less operative time and reduced risk.

The present invention in one embodiment is directed to a mesh prosthesis introducer tool for use in the laparoscopic repair of inquinal and femoral herniae. The tool is composed of a tubular housing or sheath member and a carriage member which is slideably and rotatably mounted within the sheath for axial extension and retraction, and rotation, relative to the sheath. The housing or sheath has an axially extending cavity which communicates with openings in the distal and proximal ends of the sheath. When the carriage is in the retracted position, the distal part of the carriage which comprises a holding chamber for the wound mesh is substantially contained within the cavity. While in the carriage in the retracted position, the mesh cannot unwind from the holding chamber. The carriage has an axially extending slot that communicates with the holding chamber through which the wound, radially overlapping, mesh is permitted to feed during unwinding. Since the leading edge of the mesh which extends through the slot is bounded by the cavity wall of the sheath when the carriage is retracted, the mesh cannot be fed from the holding chamber while the tholding chamber is within the cavity. When, however, the carriage is extended sufficiently so that the axially extending slot is fully extended distally from the cavity, the mesh may be fed through the slot by first fastening the leading edge of the mesh prosthesis to body tissue and then moving the carriage laterally by applying an external force to the grip cylinder located at the proximal end of the carriage.

To permit axial movement and rotation of the carriage relative to the sheath, a first silicon bearing captively carried by the sheath engages the carriage shaft adjacent the proximal opening of the sheath; a second silicon bearing carried by the carriage and in fixed relationship to the sheath bears against the cavity wall during extension and retraction of the carriage member and during the rotation of the carriage.

The sheath or housing has a radially extending shoulder at its proximal end to form a barrier to the axial advance of the housing when the sheath is inserted into an adbominal trocar. The radially extending shoulder also provides a counter-grip to permit the carriage member to be axially displaced or rotated relative to the sheath when the carrige shaft is extended or retracted or rotated.

In another embodiment of this invention, the carrige shaft contains a pair of tynes or tongs which extend axially and are located at the distal end of the carriage shaft; the tynes have an intermediate axially extending slot into which the trailing edge of the mesh prosthesis may be inserted and the mesh thereafter wound to form a radially overlapping winding about the tynes. A holding member having an axially extending cavity therethrough is so dimensioned and proportioned that the mesh prosthesis may be contained within the cavity and fed through an axially extending slot which communicates with the cavity. The holding member has a neck portion containing an axial extending bore which communicates with the cavity of the holding member and is mounted to the carriage member by a pair of roller bearings thereby permitting relative rotation between the holding member and the carriage member shaft. Thus, by rotation of the carriage member shaft the mesh prosthesis may unwind from the tynes and feed through the axial extending slot.

In another embodiment, the carriage shaft member has an axially extending channel therethrough where the channel communicates with a holding chamber located adjacent the distal end of the carriage member and communicates with an opening located at the proximal end of the carriage member thereby defining an axially extending passageway through the carriage shaft. An insertible shaft member having at its distal end a pair of axially extending tynes about which the mesh prosthesis may be radially wound and having a hinged lever at its proximal end, is unidirectionally and removeably mounted to the carriage by first extending the proximal end of the insertible member through the holding chamber of the carriage and subsequently through the passageway contained in the carriage shaft. As in the previous embodiments, the carriage member holding chamber is retractable and extendible into and from the sheath by axial movement of the carriage shaft. To unwind the mesh, the leading edge of the mesh prosthesis is fed through the axially extending slot located adjacent the distal portion of the carriage through rotation of the insertible member relative to the carriage.

Thus, in the laparoscopic repair of inquinal or femoral herniae, a tool is provided which permits the surgeon to insert a mesh prosthesis through an abdominal trocar and into the retroperitonel space while the mesh remains wound and contained in a holding chamber. Thereafter, by extending the carriage member until the leading edge of the mesh is fully extended into the operative space, the leading edge of the mesh may be laparoscopically fastened and subsequently unwound and positioned to overlay the pelvis for attachment to the abdominal wall.

BRIEF DESCRIPTION OF THE DRAWINGS

These and other features and advantages will become appreciated as the same become better understood with reference to the following specification, claims and drawings wherein:

DETAILED DESCRIPTION

Figure 1:
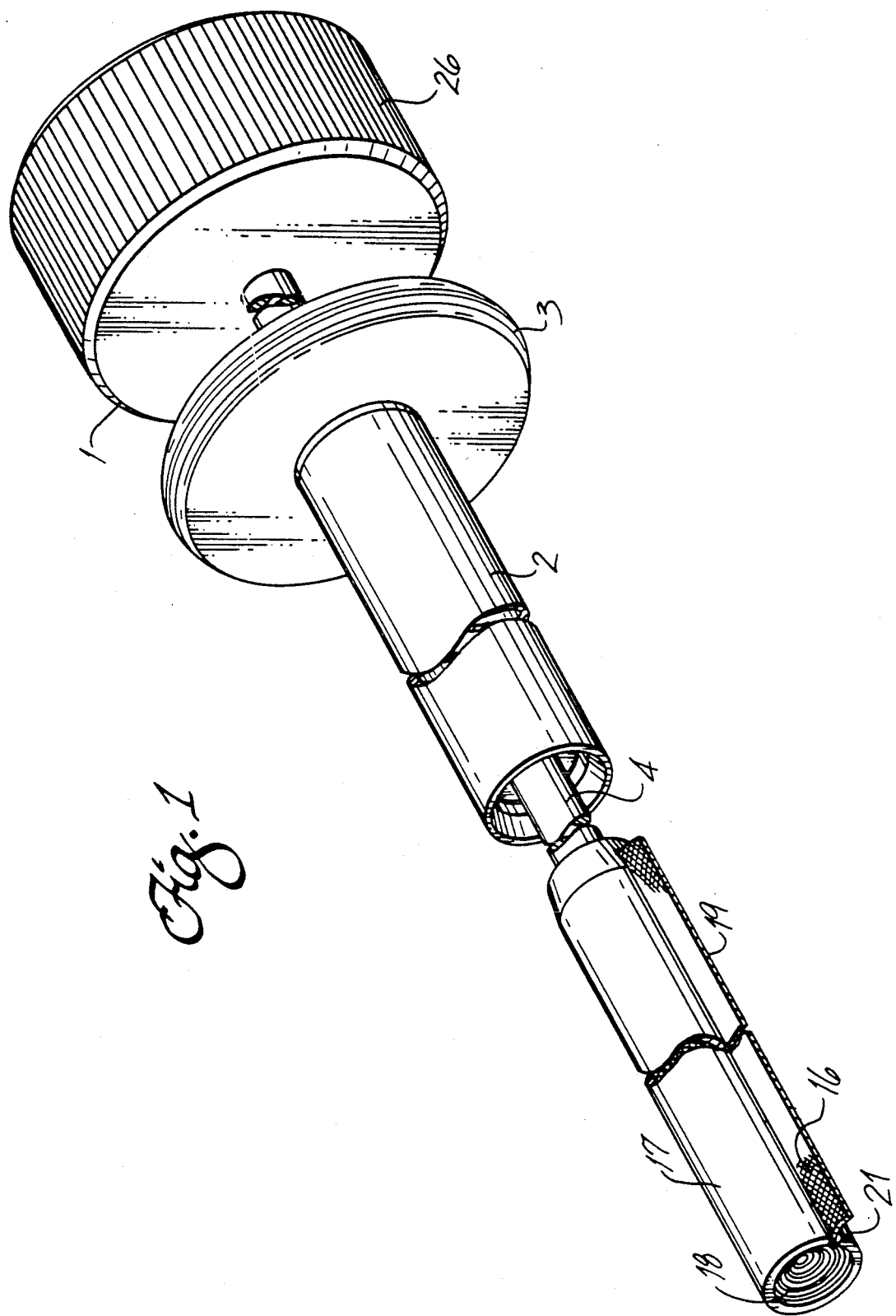
FIG. 1 is a perspective view illustrating the carriage member in an extended position with the leading edge of the wound mesh prosthesis projecting through an axially extending slot adjacent the distal end of the carriage.
Figure 3:
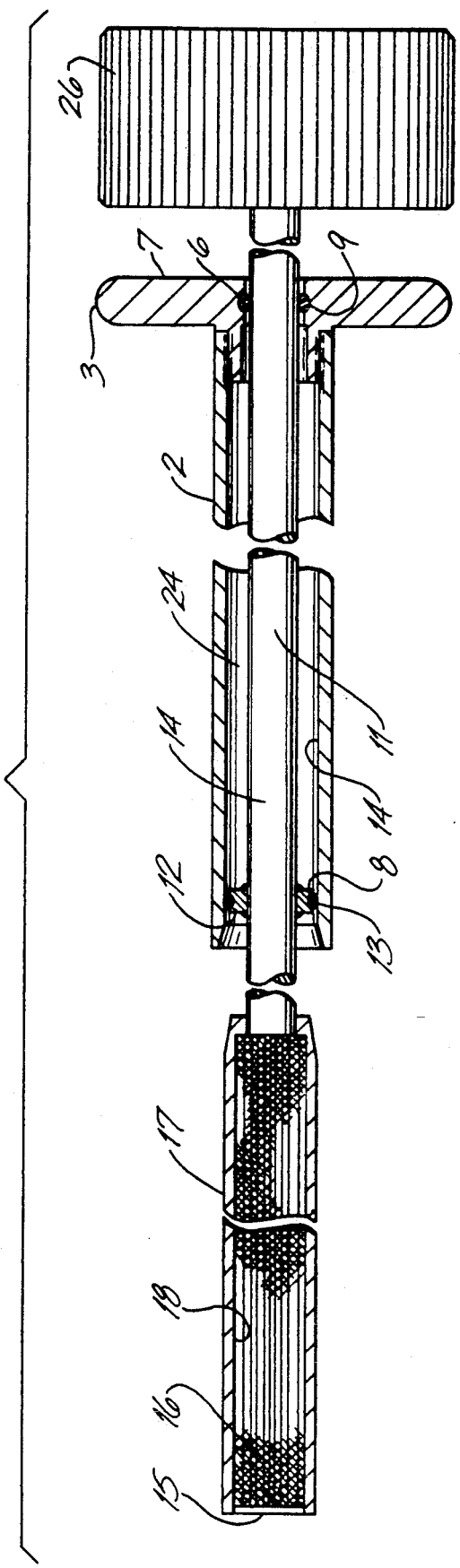
FIG. 3 is a partial cross-sectional view of FIG. 1.

Referring to FIG. 1, the mesh introducer device 1 of this invention is shown in perspective. As can be seen a housing or sheath 2 has a radially projecting shoulder 3 which limits the distance that the sheath can extend when inserted into an abdominal trocar (not shown) in order to gain access to the operative region of the patient during laparoscopic hernia repair. Carriage member 4 extends axially through the housing 2 and as illustrated in FIG. 3 is slideably mounted to the housing 2 for axial extension and retraction relative to the housing. To permit relative movement between the housing 2 and the carriage member 4, a silicon bearing 6 is carried by the housing in annular grove 9 near the distal end 7 of the housing; the carriage member 4 has a bearing member 8 carried in fixed relationship to the carriage which radially encloses carriage shaft 11 and contains an annular grove 12 for holding silicon O-ring 13 which permits relative axial movement between O-ring 13 and the inner wall 14 of the housing 2 and also permits relative rotation between the carriage and the housing.

Figure 2:
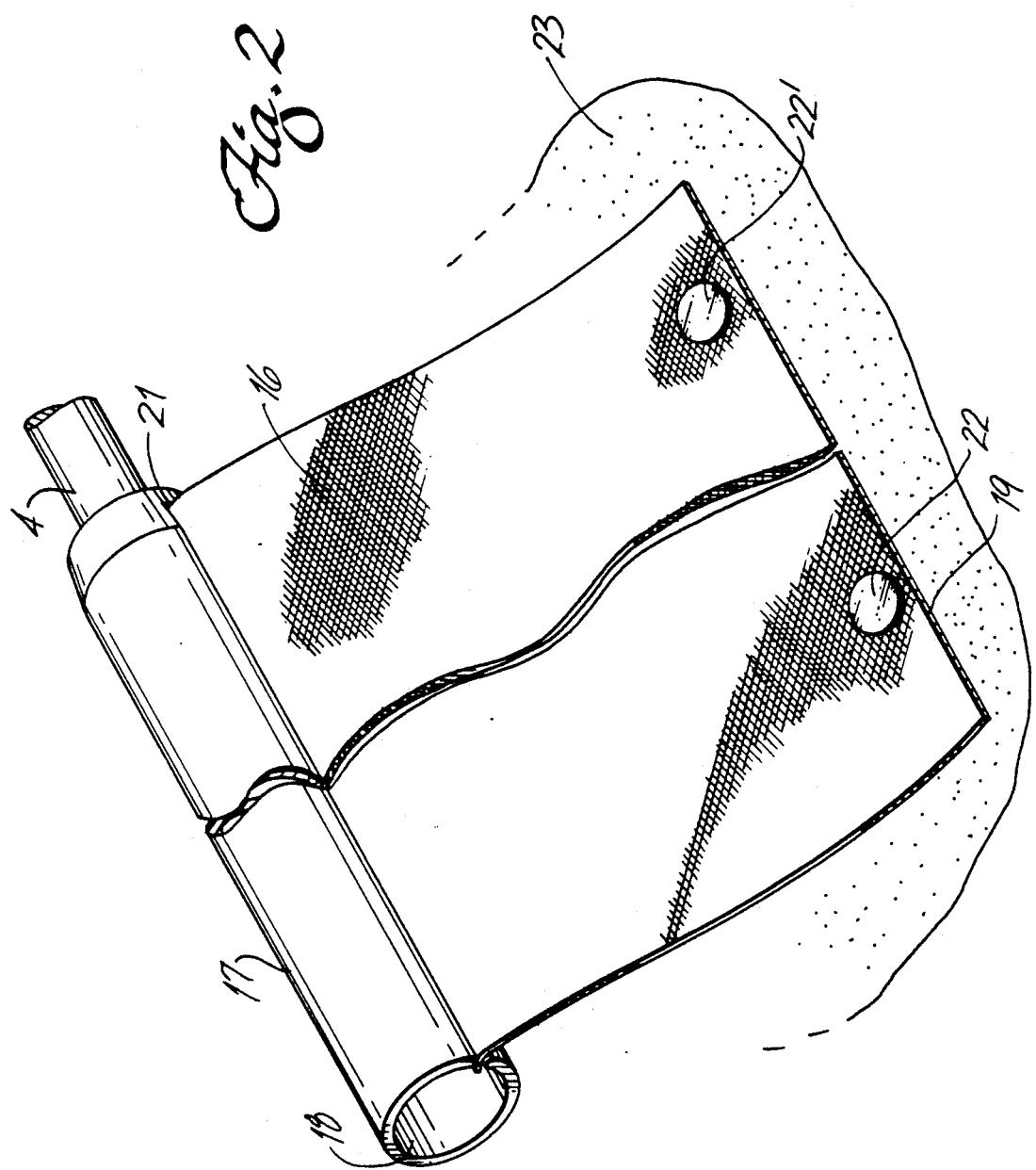
FIG. 2 is a partial perspective view of the holding chamber of the carriage member after the mesh prosthesis has been positioned and unwound from the holding chamber.

To introduce the mesh prosthesis 16, which is preferably made of a polypropylene material into the operative region of the patient's body, the carriage member 4 has a tubularly configured distal end 17 which forms the radial boundary of a holding chamber 18. The mesh prosthesis 16 is first inserted through an opening 15 located at the distal end 17 of the carriage member 4 which requires that the mesh be radially and overlappingly wound; the mesh prosthesis 16 is then held in holding chamber 18 in its radially overlap configuration with the leading edge 19 of the mesh prosthesis 16 extending through axially extending slot 21. FIG. 2 is an illustration of the mesh prosthesis 16 after having been unwound from holding chamber 18 with the leading edge 19 of the mesh prosthesis fastened to the abdominal wall 23 of the patient's body by appropriate fastening members 22 and 22'.

Referring again to FIG. 3 it can be seen that the housing or sheath 2 has a larger inner diameter than the outer diameter of the distal end 17 of the carriage member 4; this permits the retraction of the holding chamber 18 into cavity 24 of the housing or sheath 2. Thus, in the loading and operation of the mesh introducer device 1, the mesh prosthesis 16 is first wound and then inserted through opening 15 into the holding chamber of the carriage member. The leading edge 19 of the mesh prosthesis during insertion into the holding member is positioned to project through axially extending slot 21 and the holding chamber 18 is thereafter retracted into cavity 24 and completely contained within the housing 2. The leading edge of the mesh prosthesis is now bounded by inner wall 14 of the sheath and thereby the mesh prosthesis is retained in the holding chamber; the housing 2 is then inserted into an abdominal trocar (not shown) and advanced therethrough until the advancement of housing 2 within the abdominal trocar is precluded by radially projecting shoulder 3. To unwind the mesh prosthesis 16 the knurled cylinder 26 which is rigidly attached to carriage shaft 11, and in fixed relationship with the carriage shaft, is axially displaced which causes the distal end 17 of the carriage member 4 to be extended from the cavity 24 of the housing 2 into the operataive region of the patient's body; the leading edge 19 of the mesh prosthesis may now be gripped by a laparoscopic gripping tool (not shown) and extended sufficiently through axial extending slot 21 to permit the leading edge of the mesh prosthesis to be positioned for the subsequent unwinding of the mesh prosthesis and positioning to overlay the pelvis. As shown in FIG. 2, fasteners 22 and 22' are utilized to fasten the leading edge portion 19 of the mesh prosthesis to body tissue. Lateral movement of the carriage member will induce the mesh prosthesis to unwind through axial extending slot 21 until completely extended from the holding chamber after which the surgeon laparoscopically positions and fastens the mesh to body tissue to reinforce the abdominal wall thereby repairing the hernia.

Figure 4:
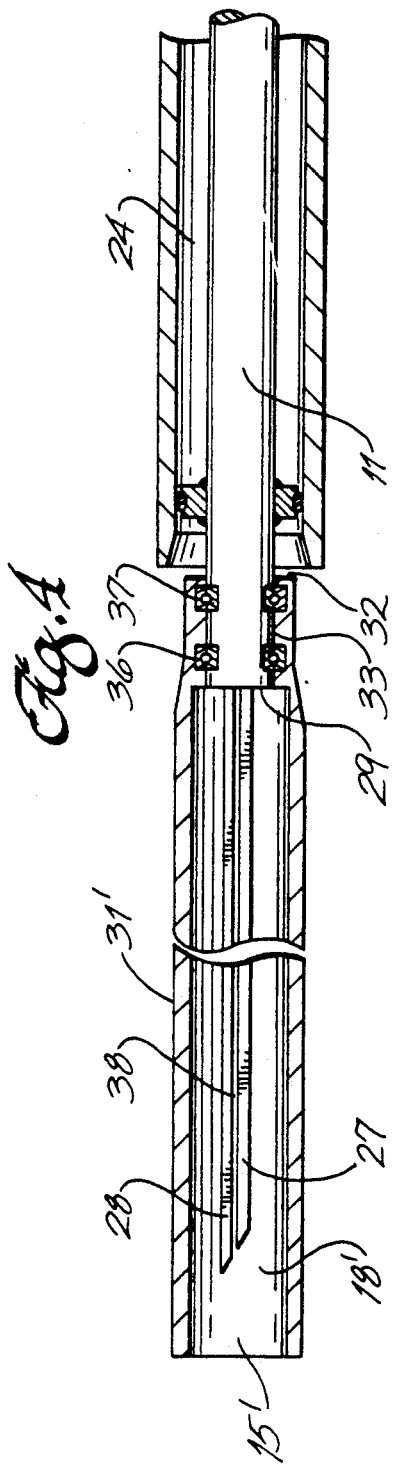
FIG. 4 is a partial cross-sectional view of FIG. 1 for another embodiment of this invention.

Another embodiment of this invention is illustrated in FIG. 4. In this embodiment, a pair of axially extending tynes 27 and 28 are fixed to and axially extend from the distal end 29 of the carriage shaft 11. A holding member 31' contains an axially extending cavity which defines a holding chamber 18' that communicates with a distal opening 15'; the proximal end 32 of holding member 31' has an axially extending bore 33 therethrough which communicates with the holding chamber 18'. Although not shown in FIG. 4, the holding member 31' also utilizes an axially extending slot through which the mesh prosthesis 16 may feed during the unwinding process of the mesh. To permit relative rotation of holding member 31 with respect to the carriage shaft 11 a pair of roller bearings 36 and 37 are utilized adjacent the distal end 29 of the carriage shaft 11. Thus, laparoscopic introduction of the mesh prosthesis into the operative region of the patient's body is accomplished by first inserting the trailing edge of the mesh prosthesis through the axially extending slot. Tynes 27 and 28 have a gap 38 between them into which the trailing edge of the mesh prosthesis is captively held and the mesh then wound radially upon the tynes into an overlapping winding by rotating the carriage shaft 11. The leading edge 19 of the mesh prosthesis is permitted to project through the axially extending slot of holding member 31' for subsequent grasping and positioning of the mesh prosthesis after the mesh has been introduced into the oprative region. By retracting carriage shaft 11, the holding member is retracted into cavity 24 of the housing. The mesh introducer device is thereafter advanced through an abdominal trocar selectively placed in the patient's abdomen and accessing the operative region. After the housing is advanced sufficiently through the trocar, as in the the embodiment above described, the radially projecting shoulder 3 of the housing which has a diameter greater than the diametric dimension of the trocar prohibits further advance of the housing relative to the abdominal trocar. By axially displacing knurled cylinder 26, the surgeon causes the carriage shaft to extend from the housing cavity 24 thereby positioning the holding member outside the sheath. The leading edge of the mesh prosthesis 19 may now be grasped by a laparoscopic grasping tool, positioned, and fasteners inserted into the body tissue as shown in FIG. 2; thereafter the mesh prosthesis is unrolled by rotating knurled cylinder 26 which rotates carriage shaft 11. During rotation of the carriage shaft, the axially extending slot contained in holding member 31' as the mesh unwinds remains nominally positioned because the unrolling and spreading of the mesh requires lateral movement of the holding member since the leading edge of the mesh has been fixed to body tissue and the mesh therefore will exert a force on the axially extending slot as it unwinds; this force is transmitted to roller bearings 36 and 37 which permits relative rotation between carriage shaft 11 and holding member 31'; thus the mesh prosthesis is allowed to feed freely through the axially extending slot as the tynes 27 and 28 are rotated and the holding member moved laterally to spread the mesh prosthesis.

Figure 5:
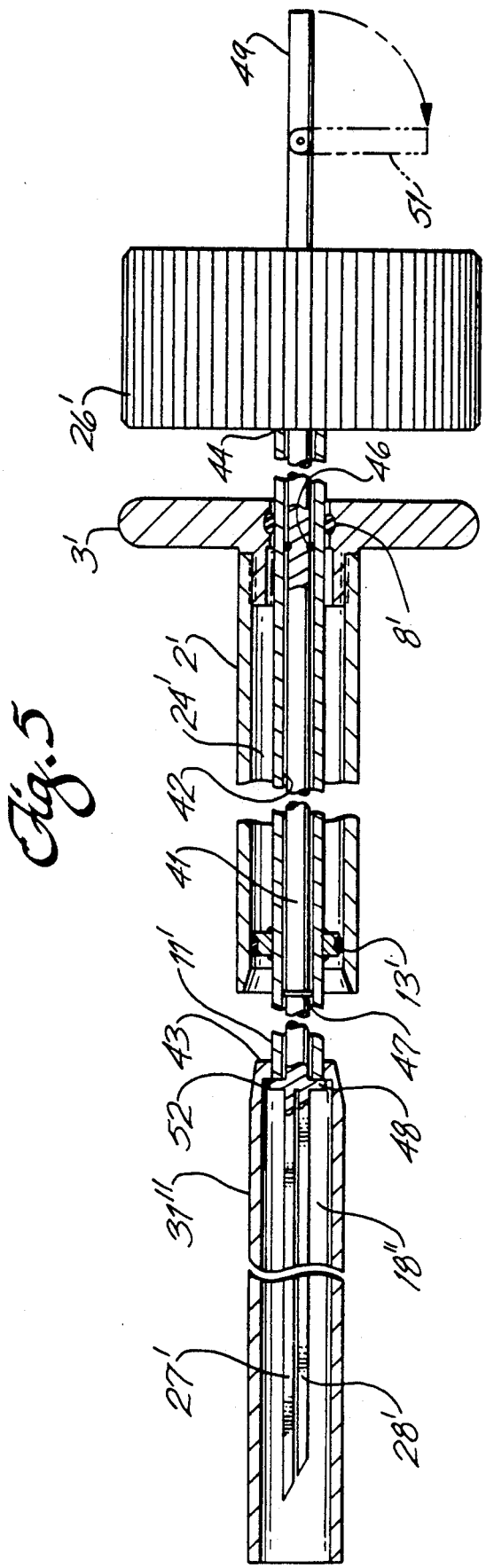
FIG. 5 is a partial cross-sectional view of FIG. 1 showing yet another embodiment of this invention.

Another embodiment of this invention is shown in FIG. 5. In this embodiment a housing or sheath 2' is illustrated having a radially projecting shoulder 3' which as in the previous embodiments acts as a barrier to prevent the further advance of the sheath 2' into an abdominal trocar (not shown). The winding and unwinding of the mesh prosthesis is accomplished by utilizing a pair of tynes 27' and 28' which extend axially from the distal end of insertible member 41. Insertable member 41 is removably mounted to housing 2' through an axially extending conduit or passageway 42 within the carriage shaft 11'. The carriage shaft 11'' is mounted in fixed relationship to holding member 31' at its proximal end 43. Carriage shaft 11' may be rotated or axially displaced by knurl cylinder 26' which is fixed to carriage shaft 11' at its proximal end 44. To permit axial extension and retraction of carriage shaft 11' and relative rotation of the carriage shaft with respect to the housing 2', the carriage shaft 11' is mounted to the housing 2' through the utilization of bearing members 8' and 13' in the same manner as in the previous embodiments. Insertible shaft member 41 carries a silicon O-rings 46 and 47; this permits insertible shaft 41 to rotate relative to passageway 42 and to provide a seal. As can be seen in FIG. 5, insertible member 41 has a radially extending flange 48 which bears against the distal end of carriage shaft 11' to limit axial movement of insertible member 41 into passageway 42 of the carriage shaft 11'. A hinged handle 51 is pivotally mounted at the proximal end 49 of insertible member 41 such that the handle 51 may be pivoted to permit rotation of the insertible member relative to the carriage shaft member 11' for the unwinding of the mesh prosthesis 16 from the tynes 27' and 28' after the holding member 31'' is extended from the housing cavity 24'. Thus, insertible member 41 is removeably carried by the housing 2' and the carriage shaft 11' to permit the mesh prosthesis to be first wound utilizing tynes 27' and 28' and thereafter inserting the proximal end 49 of the insertible member 41 through the holding chamber 18'' and into the axially extending conduit or passageway 42; the advancement of insertible member 41 through passageway or conduit 42 is limited by radially extending flange 48 abutting against the proximal inner wall 52 of holding member 31'' at the junction of inner wall 52 and the distal end of the carriage shaft 11''. In the above described embodiment, as in the previously described embodiments, when the mesh prosthesis is retracted into the holding chamber, the leading edge of the mesh prosthesis extends through the axially extending slot and is bounded by the holding chamber wall; when the holding member is extended from the cavity of the housing by extension of the carriage shaft member, unlike the previous embodiments, the tynes 27' and 28' may be rotated by rotating the insertible member which thereby feeds the mesh prosthesis through the axially extending slot.

While I have shown and described certain embodiments of the present mesh introducer device, it is to be understood that it is subject to many modifications without departing from the scope and spirit of the claims as recited herein.

What is claimed is:

1. A tool for inserting a mesh prosthesis into the retroperitoneal space in the laparoscopic repair of inquinal or femoral herniae, comprising:
   a) a housing having a proximal end and a distal end and an axis of elongation and a first opening located at said proximal end of said housing and a second opening located at said distal end of said housing, said housing having an axially extending cavity communicating with said first opening and said second opening to form a passageway therethrough;
   b) a carriage member having a proximate end and a distal end slideably carried by said housing and extending into said passageway; a holding member having an outer and inner surface carried by said carriage member and extending axially and distally from said distal end of said carriage member where said holding member has an axially extending cavity therein bounded by said inner surface and defining a holding chamber adjacent the distal end of said carriage member for holding said mesh prosthesis in a radially overlapped wound position where said holding member has an axially extending slot contained in said outer surface and communicating with said holding chamber to permit the lateral feeding of said mesh prosthesis through said slot as said mesh prosthesis radially unwinds from said holding chamber into said retroperitoneal space; and
   c) mounting means associated with said housing and said carriage member for slideably and rotatably mounting said carriage member to said housing to permit axial movement and rotation of said carriage member relative to said housing such that said holding chamber may be retracted in whole or in part into said passageway or fully extended distally of said distal end of said housing and into said retroperitoneal space.

2. The tool recited in claim 1 wherein said holding member comprises a tubular member.

3. The tool recited in claim 2 wherein said holding member is carried in fixed relationship with said carriage member.

4. The tool recited in claim 3 wherein said carriage member has an axially extending conduit therethrough communicating with said holding chamber, an insertible member having a proximate end and a distal end slideably and rotationally carried in said conduit for relative axial and rotational movement between said insertible member and said carriage member, said insertible member having a distally axially extending tyne adapted for radially winding and unwinding said mesh prosthesis laterally through said axially extending slot.

5. The tool recited in claim 4 wherein said insertible member has a hinged lever member located at the said proximate end of said insertable member, said lever member having a first position which permits said insertible member to advance within said conduit and a second position which permits said insertible member to be rotated by the application of external force to said hinged lever member.

6. The tool recited in claim 2 further comprising means associated with said carriage member and said holding member for permitting relative rotation between said carriage member and said holding member.

7. A tool for the laparoscopic repair of inquinal or femoral herniae in a retroperitoneal space comprising in combination:
a) a flexible mesh prosthesis; and
b) a housing having a proximate end and a distal end and an axis of elongation and a first opening located at said proximal end of said housing and a second opening located at said distal end of said housing, said housing having an axially extending cavity communicating with said first opening and said second opening to form a passageway therethrough, a carriage member having a proximate end and a distal end slidably carried by said housing and extending into said passageway, a holding member having an outer and inner surface carried by said carriage member and extending axially and distally from said distal end of said carriage member where said holding member has an axially extending cavity therein bounded by said inner surface and defining a holding chamber adjacent the distal end of said carriage member for holding said mesh prosthesis in a radially overlapped wound position where said holding member has an axially extending slot contained in said outer surface and communicating with said holding chamber to permit the lateral feeding of said mesh prosthesis through said slot as said mesh prosthesis radially unwinds from said holding chamber into said retroperitoneal space, and mounting means associated with said housing and said carriage member for slidably and rotatably mounting said carriage member to said housing to permit axial movement and rotation of said carriage member relative to said housing such that said holding chamber may be retracted in whole or in part into said passageway or fully extended distally of said distal end of said housing and into said retroperitoneal space.

8. The combination recited in claim 7 wherein said holding member comprises a tubular member.

9. The combination recited in claim 8 wherein said holding member is carried in fixed relationship with said carriage member.

10. The combination recited in claim 9 wherein said carriage member has an axially extending conduit therethrough communicating with said holding chamber, said combination further comprising an insertible member having a proximate end and a distal end slideably and rotationally carried in said conduit for relative axial and rotational movement between said insertible member and said carriage member, said insertible member having a distally axially extending tyne adapted for radially winding and unwinding said mesh prosthesis laterally through said axially extending slot.

11. The combination recited in claim 10 wherein said insertible member has a hinged lever member located at the proximate end of said insertable member, said lever member having a first position which permits said insertible member to advance within said conduit and a second position which permits said insertible member to be rotated by the application of external force to said hinged lever member.

12. The combination recited in claim 11 wherein said mesh prosthesis is made of polypropylene.

13. The combination recited in claim 10 wherein said mesh prosthesis is made of polypropylene.

14. The combination recited in claim 9 wherein said mesh prosthesis is made of polypropylene.

15. The combination recited in claim 8 further comprising means associated with said carriage member and said holding member for permitting relative rotation between said carriage member and said holding member.

16. The combination recited in claim 15 wherein said mesh prosthesis is made of polypropylene.

* * * * *